US006928860B1

(12) United States Patent
Hildebrandt et al.

(10) Patent No.: US 6,928,860 B1
(45) Date of Patent: Aug. 16, 2005

(54) HEAT-TRANSFER-INHIBITING MOTOR AND ROTOR

(75) Inventors: Marc J. Hildebrandt, Midland, MI (US); Richard H. Hall, Midland, MI (US); Theodore W. Selby, Midland, MI (US)

(73) Assignee: King Refrigeration, Inc., Freeland, MI (US)

(*) Notice: Subject to any disclaimer, the term of this patent is extended or adjusted under 35 U.S.C. 154(b) by 0 days.

(21) Appl. No.: 10/361,869

(22) Filed: Feb. 7, 2003

Related U.S. Application Data

(60) Provisional application No. 60/354,994, filed on Feb. 8, 2002.

(51) Int. Cl.[7] ............................................. G01N 11/14
(52) U.S. Cl. ................................................... 73/54.28
(58) Field of Search .......................... 73/54.28, 54.29, 73/54.31, 54.32, 54.33, 54.34, 54.35

(56) References Cited

U.S. PATENT DOCUMENTS

| | | | | |
|---|---|---|---|---|
| 2,227,938 A | * | 1/1941 | Krebs ............................ 374/3 |
| 2,345,968 A | * | 4/1944 | Green ........................ 73/54.22 |
| 2,503,676 A | * | 4/1950 | Marusov ..................... 73/54.09 |
| 2,834,200 A | * | 5/1958 | Rhodes et al. .............. 73/54.06 |
| 3,841,034 A | * | 10/1974 | Held ............................ 451/488 |
| 3,893,811 A | * | 7/1975 | Good et al. ................. 422/109 |
| 3,935,726 A | * | 2/1976 | Heinz ......................... 73/54.35 |
| 4,895,301 A | * | 1/1990 | Kennedy ..................... 236/34.5 |
| 5,756,883 A | * | 5/1998 | Forbes ........................ 73/54.05 |
| 5,829,754 A | * | 11/1998 | Preikschat ................... 277/408 |
| 5,971,010 A | * | 10/1999 | Kallberg et al. ............. 137/340 |
| 6,250,136 B1 | * | 6/2001 | Igreja ......................... 73/54.24 |
| 6,282,948 B1 | | 9/2001 | O'Dell et al. | |

FOREIGN PATENT DOCUMENTS

| | | | | |
|---|---|---|---|---|
| DE | 1532957 B | * | 6/1971 | ........... A21C 00/00 |
| DE | 2728173 A | * | 1/1979 | ............. C22B 9/02 |
| JP | 57117334 A | * | 7/1982 | .............. B01J 8/38 |
| JP | 05298813 A | * | 11/1993 | ........... G11B 19/20 |
| JP | 07067286 A | * | 3/1995 | ............. H02K 7/00 |
| JP | 11109089 A | * | 4/1999 | ........... G21C 21/02 |
| SU | 1803623 A1 | * | 3/1993 | ........... F16C 37/00 |

OTHER PUBLICATIONS

Hildebrandt et al., U.S. Appl. No. 60/354,994 filed Feb. 8, 2002.
Selby, U.S. Appl. No. 08/490,111 filed Jun. 6, 1995.

* cited by examiner

*Primary Examiner*—Charles Garber
(74) *Attorney, Agent, or Firm*—Christopher John Rudy

(57) ABSTRACT

Heat-inhibition respecting a motor is provided in connection with a heated instrument through a stand-off mount system and/or a heat-inhibiting rotor/stirrer. The instrument can be a hot bath containing instrument where stirring of the contents of the bath can be carried out, for example, a kinematic viscosity bath device, which may include the stand-off mount system and heat-inhibiting rotor/stirrer in which is present a convoluted path for heat conduction and/or increased air flow generator between the surface of the bath and the motor.

18 Claims, 2 Drawing Sheets

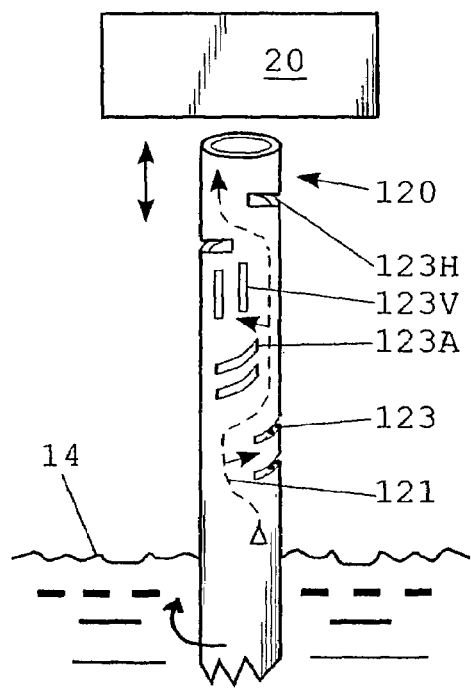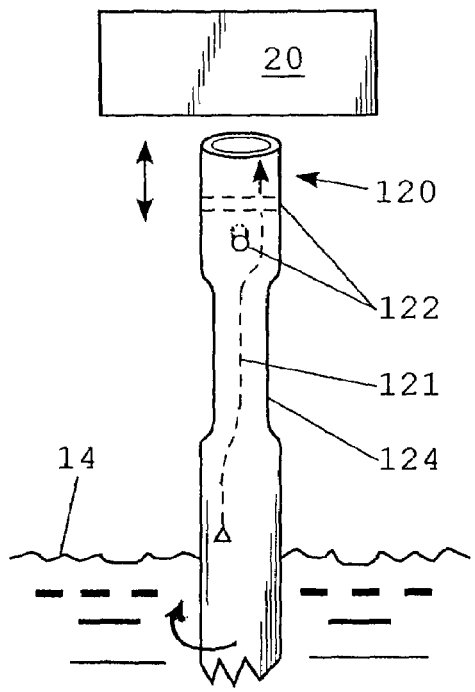
Fig. 2A    Fig. 2B
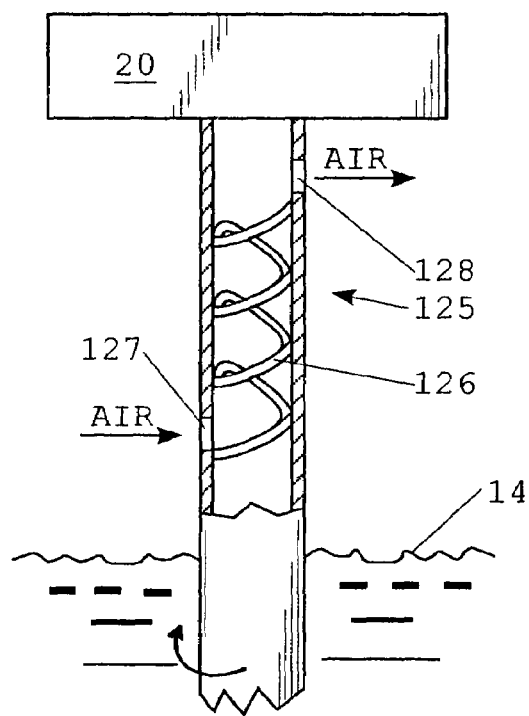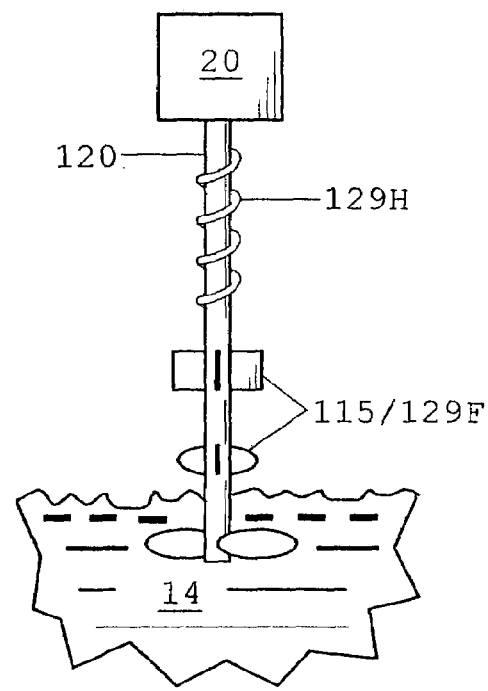
Fig. 3    Fig. 4

HEAT-TRANSFER-INHIBITING MOTOR AND ROTOR

This claims 35 USC 119(e) benefit of U.S. provisional patent application No. 60/354,994 filed Feb. 8, 2002 A.D. The complete specification of the same is incorporated herein by reference.

BACKGROUND TO INVENTION

I. Field and Purview

The present invention concerns heat-inhibition with respect to a motor, and the same in connection with a heated instrument.

II. Art with Problems

In kinematic viscosity baths, a tank of mineral oil is heated to provide control for samples immersed therein for determination of kinematic viscosity, and the mineral oil is stirred to provide uniform heating of the samples. It is a simple device, indeed, and owing to its simplicity and the nature of testing involved in the art, economy is a prime consideration in providing the baths.

In prior baths, the rather inexpensive stirring motor, which was mounted directly to a top panel on the kinematic viscosity bath cabinet, would fail prematurely owing to overheating from transfer of heat from the bath during testing. One solution is to purchase and install another model of motor rated to withstand the 150-degree C. temperature of the test, but such an alternate motor involves a roughly five- to ten-fold increase in cost compared to the more economically priced motor. Thus, the consideration of economy in providing the test would be lost.

It would be desirable to ameliorate if not overcome the same.

SUMMARY OF INVENTION

The present invention provides heat-inhibition with respect to a motor, and the same in connection with a heated instrument. In particular, it provides for a stand-off mount system and/or a heat-inhibiting rotor/stirrer. It especially provides for the stand-off mount system and/or a heat-inhibiting rotor/stirrer in a hot bath containing instrument where stirring of the contents of the bath can be carried out. For example, the instrument can be a kinematic viscosity bath device, which may include the stand-off mount system and heat-inhibiting rotor/stirrer in which is present a convoluted path for heat conduction and/or increased air flow generator between the surface of the bath and the motor.

The invention is useful in conserving motors and in testing.

Significantly by the invention rotating electric motors which power stirrers in hot bath devices can be saved by damage caused by the transfer of heat in excess of the rated capacity of the motor. In turn, less expensive, lower heat-rated motors can be employed. Thus, for example, a prime consideration of economy in providing the kinematic viscosity bath test is not compromised, and testing can be carried out economically while retaining accuracy. Numerous further advantages attend the invention.

DRAWINGS ILLUSTRATIVE OF INVENTION

The drawings form part of the specification hereof. With respect to the drawings, which are not necessarily drawn to scale, the following is briefly noted:

FIGS. 2A and 2B are plan views of rotor/stirrers of the invention, each showing a convoluted path for heat conduction.

FIG. 3 is a side part-sectional view of another rotor/stirrer of the invention, showing an increased air flow generator.

FIG. 4 is a side plan view of another rotor/stirrer of the invention, showing external, increased air flow generators.

DETAILED DESCRIPTION ILLUSTRATIVE OF INVENTION

Figure 1:
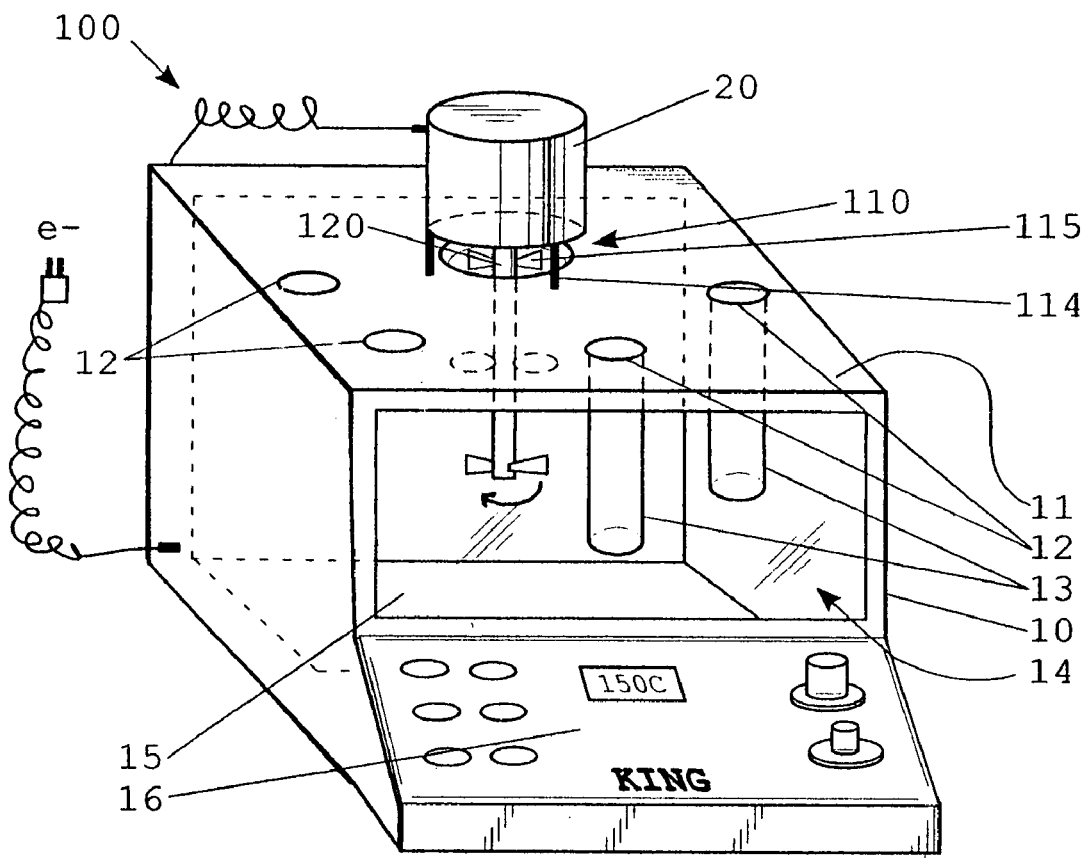
FIG. 1 is a perspective plan view of a kinematic viscosity bath modified according to the practice of the present invention.

The invention can be further understood by the present detail, which may be read in view of the drawings. Such is to be taken in an illustrative and not necessarily limiting sense.

In general, a motor is inhibited from excessive heat. Such can be found as part of a heated instrument. To accomplish this, a stand-off mount system, heat-inhibiting rotor/stirrer, or both, can be provided the motor. Hot bath containing instruments where stirring of the contents of the bath is carried out by a rotating electric motor especially are beneficially modified with the stand-off mount system and/or heat-inhibiting rotor/stirrer.

With respect to the drawings, instrument 100 in the form of a kinematic viscosity bath device includes cabinet 10, with top 11; sample ports 12, which hold test sample containers 13, each with liquid sample; heated mineral oil bath 14; observation window 15; control and display panel 16; and rotating electric stirring motor 20 above access hole 21. The motor 20 is mounted to the top 11 by stand-off mount system 110, particularly embodied by a plurality, say, three to six, for example, four, elongate posts 114. The posts 114 can be made of any suitable material, but preferably are such that heat is insulated from or dissipated before it would be conducted to the motor. Thus, heat-insulating rubber or plastic, or a metal which dissipates heat to the atmosphere by itself or through such modifications as being provided with a convoluted path akin to that described for the rotor/stirrer, or fins, upon which air may be blown through fan blades 115 placed on the upper portion of motor rotor/stirrer 120 or through other means such as an external fan or air draft. The stirrer 120 can be a hollow, elongate, heat-inhibiting, steel rotor/stirrer having convoluted path 121 for heat conduction provided from holes 122 and/or cuts 123, whether angled 123A, horizontal 123H or vertical 123V. The holes 122 and cuts 123 beneficially penetrate the stirrer 120 to its hollow interior. A simple constriction 124 may also be provided in this connection. Alternatively or in addition, the heat-inhibiting in the stirrer 120 can provided by increased air flow generator 125, for example, interior helical air screw 126, say, from a flat band, helical spring, with the rotor/stirrer 120 having lower hole 127 and upper hole 128 for ingress or egress of air, can cool the rotor/stirrer 120. Rotation of the stirrer 120 in one direction, for example, clockwise looking from the top, moves the air from the lower hole 127 to the upper hole 128, and counterclockwise rotation moves the air oppositely. An external, increased air flow generator 129 such as another fin or type of fin 115, 129F (lower) or external helical air screw 129H may be put on the outside of the rotor/stirrer 120. The pathway 121 and air flow generator 125 are between the upper surface of the oil in the bath 14 and the motor 20.

CONCLUSION TO INVENTION

The present invention is thus provided. Various features, parts, subcombinations of combinations can be employed with or without reference to other features, parts, subcombinations and combinations in the practice of the invention, and numerous and sundry adaptations and modifications can be effected within its spirit, the literal claim scope of which is particularly pointed out as follows:

We claim:

1. In a hot bath containing laboratory instrument for measurement of kinematic viscosity of a test sample in a test sample container separate from but immersed in liquid contents of a hot bath having an upper surface where stirring of the contents of the bath can be carried out through use of a motor that rotates a stirrer of the hot bath and that is mounted to a top of the instrument, the improvement which comprises a heat-inhibiting rotating stirrer such that heat is inhibited from passing between the surface of the bath and the motor, wherein the heat-inhibiting rotating stirrer is provided with at least one of a convoluted path for heat conduction between the upper surface of the bath and the motor and an increased air flow generator between the surface of the bath and the motor.

2. The improvement of claim 1, wherein a stand-off mount system is present and embodied by a plurality of elongate posts.

3. The improvement of claim 2, wherein an internal helical air screw is present as the increased air flow generator.

4. The improvement of claim 2, wherein an increased air flow generator by said internal helical air screw and by an external helical air screw are present.

5. The improvement of claim 1, wherein the heat-inhibiting rotating stirrer has at least one of the convoluted path for heat conduction between the upper surface of the bath and the motor and an increased air flow generator by an external helical air screw between the surface of the bath and the motor.

6. The improvement of claim 5, wherein said external helical air screw is present.

7. The improvement of claim 1, wherein the heat-inhibiting rotating stirrer is elongate and has a hollow interior, and has a convoluted path for heat conduction.

8. The improvement of claim 7, wherein the heat-inhibiting rotating stirrer is made of steel.

9. The improvement of claim 8, wherein said convoluted path is provided from at least one of holes and cuts which penetrate to the hollow interior of the heat-inhibiting rotating stirrer.

10. The improvement of claim 9, wherein the at least one of holes and cuts includes cuts that are at least one of angled, horizontal and vertical.

11. The improvement of claim 7, wherein said convoluted path is provided from at least one of holes and cuts which penetrate to the hollow interior of the heat-inhibiting rotating stirrer.

12. The improvement of claim 11, wherein the at least one of holes and cuts includes cuts that are at least one of angled, horizontal and vertical.

13. The improvement of claim 1, wherein the heat-inhibiting rotating stirrer is elongate and has a convoluted path for heat conduction provided by a constriction.

14. The improvement of claim 1, wherein the heat-inhibiting in the heat-inhibiting rotating stirrer is provided by an increased air flow generator by an interior helical air screw.

15. The improvement of claim 14, wherein the interior helical air screw is provided by a flat band, helical spring, with the heat-inhibiting rotating stirrer having a lower hole and an upper hole for ingress or egress of air.

16. In a hot bath containing laboratory test instrument for measurement of viscosity of a test sample in a test sample container separate from but immersed in liquid contents of a hot mineral oil bath having an upper surface where stirring of the contents of the bath can be carried out through use of a rotating electric motor that rotates a stirrer of the hot bath, the improvement which comprises a stand-off mount system such that heat is insulated from or dissipated before it would be conducted to the motor that is mounted to the top by the stand-off mount system, and a heat-inhibiting rotating stirrer, which is elongate and has a hollow interior, and has a convoluted path for heat conduction between the upper surface of the bath and the motor such that heat is inhibited from passing between the surface of the bath and the motor.

17. The improvement of claim 16, wherein the heat-inhibiting rotating stirrer has at least one of holes and cuts that penetrate to its hollow interior to provide the convoluted path.

18. In a hot bath containing instrument where stirring of the contents of the bath can be carried out through use of a motor, the improvement which comprises a heat-inhibiting rotating stirrer, wherein at least one of the following is present:

the rotating stirrer has an increased air flow generator by an internal helical air screw and by an external helical air screw; and the heat-inhibiting in the rotating stirrer is provided by an increased air flow generator by an interior helical air screw, which is provided by a flat band, helical spring, with the rotating stirrer having a lower hole and an upper hole for ingress or egress of air.

* * * * *